(12) United States Patent
Gardeski

(10) Patent No.: US 7,101,361 B2
(45) Date of Patent: Sep. 5, 2006

(54) STEERABLE MEDICAL DEVICE HAVING MEANS FOR IMPARTING CURVES IN THE DEVICE AND IN ELONGATED IMPLANTABLE MEDICAL INSTRUMENTS

(75) Inventor: Kenneth C. Gardeski, Plymouth, MN (US)

(73) Assignee: Medtronics, Inc., Minneapolis, MN (US)

( * ) Notice: Subject to any disclaimer, the term of this patent is extended or adjusted under 35 U.S.C. 154(b) by 594 days.

(21) Appl. No.: 10/318,626

(22) Filed: Dec. 16, 2002

(65) Prior Publication Data

US 2004/0116849 A1 Jun. 17, 2004

(51) Int. Cl.
*A61M 25/00* (2006.01)

(52) U.S. Cl. ..................................... 604/523; 604/95.01
(58) Field of Classification Search ............. 604/96.01, 604/523, 524, 525, 526, 527, 528, 264; 606/191–194
See application file for complete search history.

(56) References Cited

U.S. PATENT DOCUMENTS

| | | |
|---|---|---|
| 4,136,703 A | 1/1979 | Wittkampf |
| 4,381,013 A | 4/1983 | Dutcher |
| 4,676,249 A | 6/1987 | Arenas et al. |
| 4,815,478 A | 3/1989 | Buchbinder et al. |
| 4,898,577 A | 2/1990 | Badger et al. |
| 4,940,062 A | 7/1990 | Hampton et al. |
| 5,040,543 A | 8/1991 | Badera et al. |
| 5,170,787 A | 12/1992 | Lindegren |
| 5,327,906 A | 7/1994 | Fideler |
| 5,342,371 A * | 8/1994 | Welter et al. ................ 606/113 |
| 5,439,006 A | 8/1995 | Brennen et al. |
| 5,545,200 A | 8/1996 | West et al. |
| 5,662,119 A | 9/1997 | Brennen et al. |
| 5,728,148 A | 3/1998 | Bostrom et al. |
| 5,797,856 A * | 8/1998 | Frisbie et al. ................ 600/585 |
| 5,921,971 A * | 7/1999 | Agro et al. .................. 604/523 |
| 6,027,462 A | 2/2000 | Greene et al. |
| 6,059,739 A | 5/2000 | Baumann |
| 6,146,338 A | 11/2000 | Gardeski et al. |
| 6,251,092 B1 | 6/2001 | Qin et al. |
| 6,280,433 B1 | 8/2001 | McIvor et al. |
| 6,379,346 B1 | 4/2002 | McIvor et al. |

* cited by examiner

*Primary Examiner*—Manuel Mendez
(74) *Attorney, Agent, or Firm*—Girma Wolde-Michael; Michael C. Soldner

(57) ABSTRACT

A steerable elongated medical device adapted to be advanced through a tortuous pathway to a desired location in a body includes an outer tube extending between an outer tube proximal segment and an outer tube distal segment, having an outer tube wall forming an outer tube lumen and an elongated outer tube slot through the outer tube wall to the outer tube lumen. The elongated outer tube slot has a first portion and a second portion and is formed between an outer tube slot proximal end and an outer tube slot distal end and extending axially along the outer tube distal segment through an outer tube slot length to define a cutaway portion of the outer tube. A reinforcing sleeve is positioned within the outer tube lumen and extends between a reinforcing sleeve proximal end and a reinforcing sleeve distal end, and the reinforcing sleeve forms a reinforcing sleeve slot portion aligned with and extending along the first portion of the outer tube slot and includes a reinforcing sleeve overlap portion extending over the second portion of the outer tube slot.

16 Claims, 4 Drawing Sheets

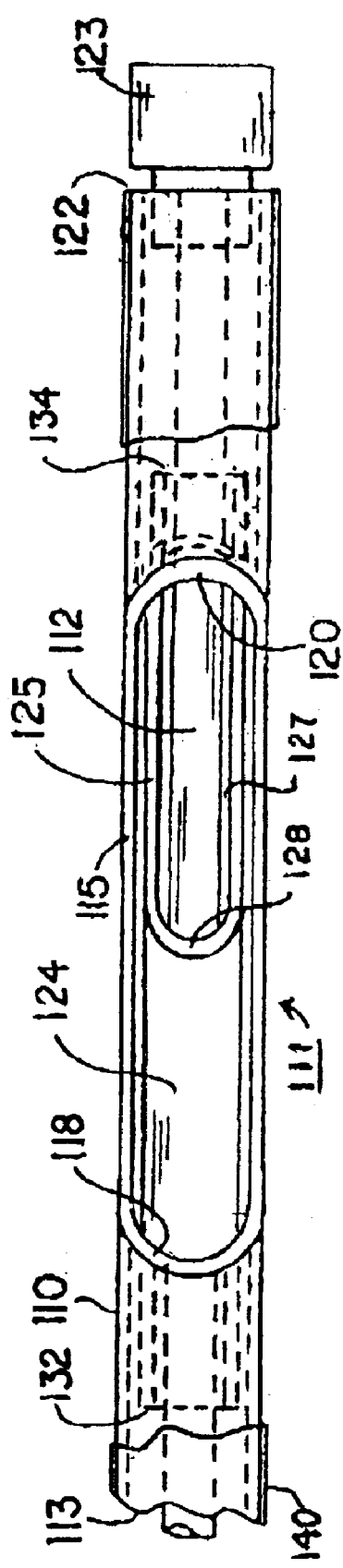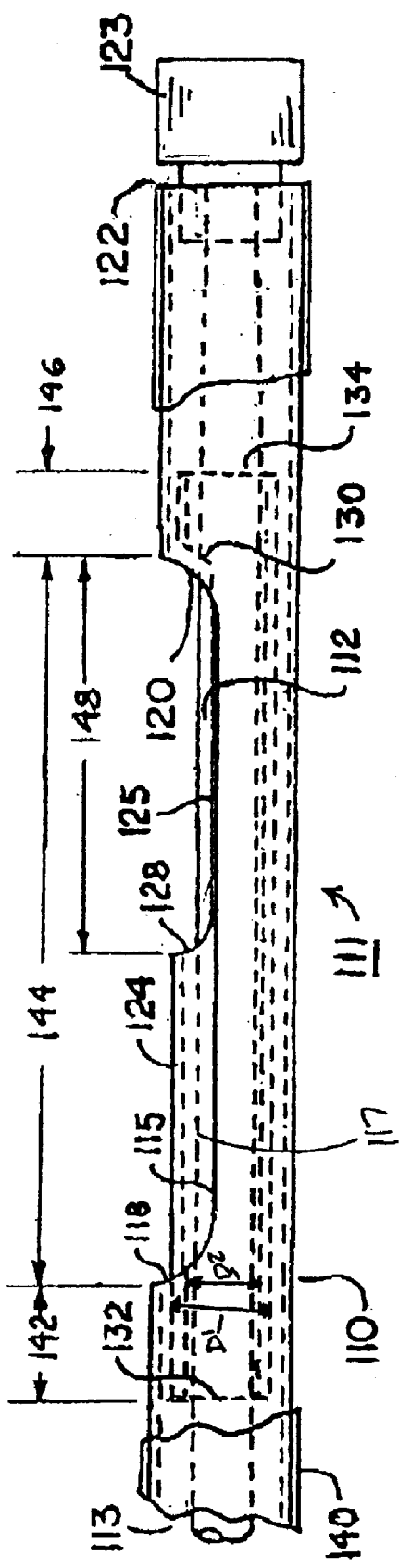

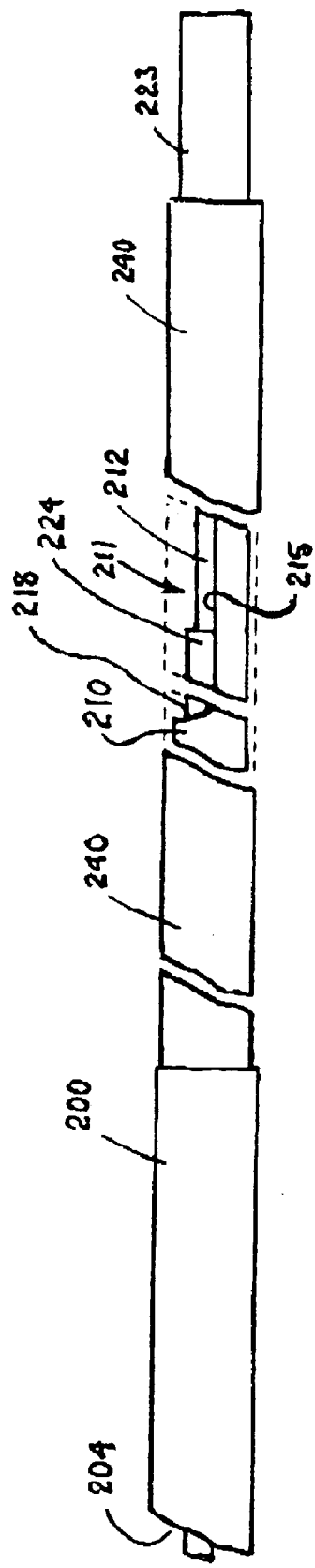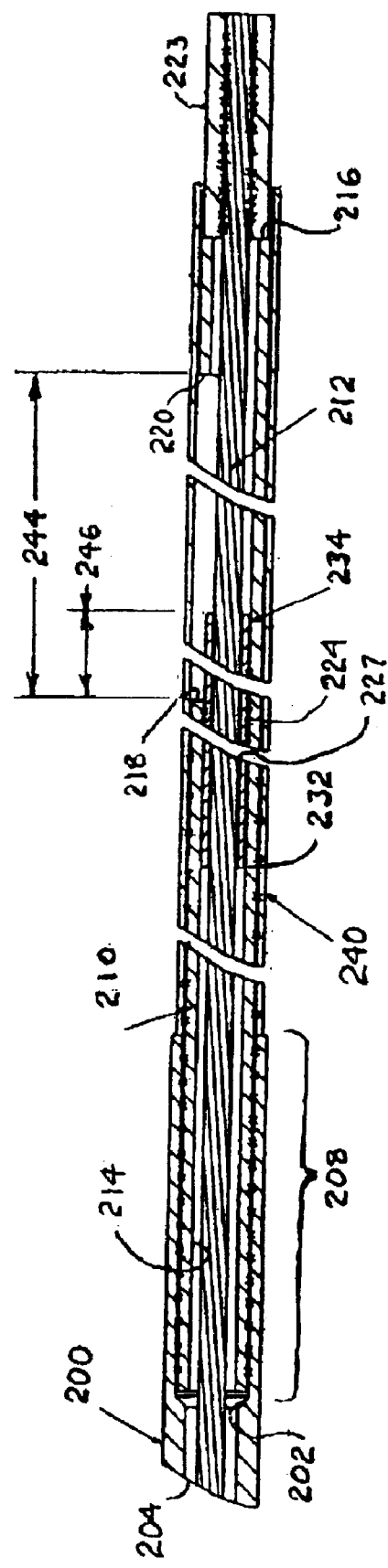
FIG. 7
FIG. 8

STEERABLE MEDICAL DEVICE HAVING MEANS FOR IMPARTING CURVES IN THE DEVICE AND IN ELONGATED IMPLANTABLE MEDICAL INSTRUMENTS

FIELD OF THE INVENTION

The present invention pertains to the permanent or temporary implantation of elongated medical instruments in the body or used to access a site in the body to facilitate introduction of a further medical device, and particularly to elongated steerable medical devices, such as a steerable stylets, for steering the distal end and imparting curves in distal segments of such medical instruments to facilitate implantation.

BACKGROUND OF THE INVENTION

A wide variety of elongated medical instruments are currently available that are adapted to be permanently or temporarily implanted in the mammalian body, usually the body of a human patient, or used to access a site in the body to facilitate introduction of a further implantable medical device or delivery of a therapeutic or diagnostic agent. Such elongated medical instruments have an instrument body extending between instrument body proximal and distal ends, and a distal segment of the instrument body is advanced to a remote site in the body.

In many cases, the introduction of such elongated medical instruments to a remote site in the body is effected through a skin incision accessing an incision into a blood vessel, whereby the instrument body is advanced through a pathway until the distal segment or the instrument body distal end are located at the remote site. Such advancement is often through a tortuous pathway having twists and turns requiring the capability to impart a curve or deflect the instrument body distal end to facilitate advancement. Therefore, the introduction of such elongated medical instruments through vascular pathways or other tortuous pathways in the body is facilitated by a wide variety of techniques and mechanisms that have been developed to impart curves in the distal segment of the instrument body or to deflect or steer the instrument body distal end.

Currently, endocardial cardiac pacing leads used in association with a pacemaker implantable pulse generator (IPG) and/or cardioversion/defibrillation leads used in association with implantable cardioverter/defibrillator (ICD) IPGs are introduced into a vein either via a cut down or percutaneous sheath introduction. Such cardiac leads are advanced under fluoroscopy into either the right atrium, right ventricle (or both in the case of a dual chamber pacemaker or ICD implantation) or into a cardiac vessel, e.g., the coronary sinus and great vein. Generally speaking, it is highly desirable that such cardiac leads be so flexible through their length that they are capable of flexing with the movement of the heart and other muscular movement so as to void the fracture of the lead body due to its cumulative stressing. Such cardiac lead bodies are generally too limp to be advanced axially on their own through the vascular pathway to the desired site in a heart chamber or vessel.

It has been commonplace for many years to employ thin wire, stiffening stylets extended down a lumen of the lead body to stiffen the entire assembly so that it can be pushed axially through the venous pathway. Then, the distal pace/sense electrodes or cardioversion/defibrillation electrodes (herein "cardiac electrodes") must be fixed at the preferred site in the heart chamber or vessel to operate most efficaciously and to prevent dislodgement. The introduction and fixation of these cardiac leads is the most time consuming and difficult aspect of the implantation.

At the outset, a straight or slightly curved stiffening stylet wire is first extended into the lead body lumen within the cardiac lead in order to give the cardiac lead sufficient column strength and rigidity to be pushed through the tributary veins and typically into the subclavian vein. The stylet wire may be left straight or provided with a certain degree of curvature to facilitate the introduction through these veins and through the initial curvatures thereof. Thereafter, and from time to time, as the physician directs the distal tip of the cardiac lead in a tortuous path leading to the right heart through the superior vena cava (SVC), it may be necessary to withdraw the stylet and either substitute a new stylet wire or impart a different curvature to the distal portion of the stylet wire, reinsert the stylet wire, and advance the distal portion of the lead a bit further until another obstacle to advancement is encountered.

When the distal cardiac electrodes are to be placed in the right ventricle, the physician manually fashions a curve at the tip of another stylet wire that is inserted into the lead body lumen to advance the assembly through the tricuspid valve into the right ventricle. Most physicians continue advancing the lead with the curved tip stylet in place into the pulmonary artery outflow track to confirm right ventricle access and to rule out the possibility of entrance into the coronary sinus or coronary vein, which can mimic the appearance of a right ventricle placement under fluoroscopy. The conventional practice requires the physician to then remove the curved stylet and partially re-advance the original or another straight stylet into the lead body lumen, once the physician has confirmed that the lead is in fact in the pulmonary outflow track. The cardiac lead is then carefully pulled back under direct fluoroscopic observation until the lead body distal segment drops from the proximal portion of the pulmonary artery to the floor of the right ventricle. The physician then advances the stylet to its fully advanced position within the lead body lumen and advances the lead distal end into the right ventricular apex. Passive or active fixation mechanisms at the lead body distal end then effect fixation with the trabeculae or the myocardium to acutely maintain the cardiac electrode electrode(s) at the operative site.

In the case of atrial lead placement, the lead body distal end is typically lodged or affixed in the right atrial appendage which results in the lead body extending into the right atrium via the SVC and then bent through about a 180° or greater bend. Over the years, many atrial cardiac lead designs and atrial cardiac lead introduction tools and techniques have been proposed or clinically used to both achieve this orientation and to fix the cardiac lead body distal end within the atrial appendage and avoid dislodgement. Initially, such atrial cardiac leads were formed with a permanent "J"-shaped bend to facilitate both the positioning and the retention of the atrial electrode in the patient's atrial appendage as taught, for example, in U.S. Pat. No. 4,136,703. Insertion of these "J"-shaped leads is greatly facilitated through the use of a straight solid inner stylet which, in this case, straightens the bend normally fixed within the distal end of the lead itself to the extent that the stylet is advanced into or retracted from the lead body lumen. Such J-shaped atrial leads have largely been abandoned in favor of reduced diameter lead bodies that cannot accommodate shape-forming structures and the use of the straightening stylet as described above. Today, the small diameter cardiac lead body is normally straight, and the lead body distal end is typically aimed into the atrial appendage employing multiple insertions of relatively straight and curved stylets. The electrode bearing lead body distal end is fixed in the atrial appendage by means of an active fixation screw or passive fixation tines. However, dislodgements can occur before the fixation is effected when a stylet is withdrawn proximally as the stylet may bind against the lead body lumen in the region of the bend.

Similar techniques and multiple stylets are avoided to advance a cardiac lead distal segment into the coronary sinus and great vein.

Thus, there are multiple exchanges of straight stylet wires and curved stylet wires which have been bent according to the physician's choice in a typical cardiac lead implantation in the right atrium and ventricle. Stylets are typically formed of solid wire, typically about 0.014–0.018 inches in diameter. During handing, such stylets can easily become bent or kinked, and thereafter cause great difficulty when an attempt is made to reinsert them through the narrow inner diameter of the lead body lumen, which may only be 0.019 inch in the case of a stylet of 0.018 inch diameter, thereby providing no more than 0.0005 inch clearance around the circumference. The continual withdrawal and reintroduction of stylets is time consuming and offers the potential of damaging the lead in the process.

Moreover, it is undesirable to contaminate the lead body lumen with blood during this process because drying blood can form a strong adhesive bond between the stylet and the lumen wall, making stylet removal impossible and rendering the lead unusable. Because the surgeon is working through an open wound, even the most fastidious surgeon will have blood on his gloves that can be transferred to the stylet. The blood congeals, and because of the small clearance, even a few drops of blood are sufficient to causing jamming of the stylet inside the lead body lumen. When the stylet jams in the lead body lumen, kinking of the stylet within the lead can occur, which kinks, in turn, will create new jams or problems with the insertion and retraction of the stylet from the lead body lumen. In some cases, the jamming is so severe that the cardiac lead must be removed from the heart for fear of insulation puncture, discarded, and a new lead implanted, thereby at least doubling the lead cost used in the procedure as well as operative time. The overall result of such difficulties is that operative time is greatly increased, which results in increased time delay, associated cost, and prolonged X-ray exposure to the patient under continuous fluoroscopy as well as prolonged scattered X-ray exposure to the operating room staff due to procedural time delays. These problems with the use of multiple stiffening stylets have been recognized in the art and many proposals have therefore been advanced to reduce the number of stylets and the consequent number of times that stylet removal and re-insertion are needed.

In addition, the complexity of cardiac leads, the number of cardiac leads implanted in a common path, and the advancement of coronary sinus leads deep in a coronary vein have led to efforts to at least not increase and optimally to decrease the overall diameter of the cardiac lead body without sacrificing reliability and usability. More recently, it has been proposed to diminish the lead body by eliminating the lumen for receiving the stiffening stylet and by reducing the gauge and coil diameter of the coiled wire conductor or replacing it with highly conductive stranded filament wires or cables. In bipolar or multi-polar leads, each such cable extends through a separate lumen of the lead body to maintain electrical isolation.

Over the last 30 years, it has become possible to reduce endocardial lead body diameters from 10 to 12 French (3.3 to 4.0 mm) down to 2 French (0.66 mm) presently through a variety of improvements in conductor and insulator materials and manufacturing techniques. The lead bodies of such small diameter, 2 French, endocardial leads must possess little if any column strength that could cause the lead distal end fixation mechanism and electrode to perforate through the myocardium during implantation and if the lead body were to become axially force-loaded during chronic implantation. As a result, the small diameter lead bodies lack "pushability", that is the ability to advance the lead distal end axially when the lead proximal end is pushed axially, particularly when the lead body extends through the tortuous transvenous pathway.

Commonly assigned U.S. Pat. Nos. 6,280,433 and 6,379,346 disclose steerable catheters that are employed to access a blood vessel through a percutaneous incision and to be advanced to a site within the vascular system or a heart chamber so that such a small diameter cardiac lead can be implanted through a delivery lumen of the catheter. A bilumen catheter body is disclosed that includes a relatively large diameter delivery lumen and a smaller diameter stylet lumen that is blocked at its distal end. The deflection mechanism in this case includes a stiffening stylet that can be selectively introduced into and removed from the stylet lumen from a proximal hub or handle. The stiffening stylet is advanced distally until the stylet distal end abuts the closed stylet lumen distal end to stiffen the catheter body to aid its introduction and advancement. The stylet distal end can be shaped when outside the stylet lumen opening to impart a curve to the catheter body when inserted into the lumen to assist in steering the catheter body distal end through the pathway. The stylet lumen is preferably lined with a wire coil sheath, and the handle and delivery lumen are preferably slittable by a slitting tool to aid in removing the introducer catheter from an electrical medical lead introduced through the delivery lumen. The delivery lumen exit port and the closed end of the stylet lumen are both located at the bitumen catheter body distal end.

A variety of deflectable or steerable stylets have been proposed and in some cases clinically introduced to aid in direct implantation of a cardiac lead having a lead lumen or to aid in the deflection and steering of a bilumen guide catheter. One approach has been to employ deflectable stylets wherein the stylet distal segment can be deflected or curved while within the lead body lumen from the proximal end thereof. Two-piece stylets that include a straight, tubular outer member and a curved inner member received within the outer member lumen enabling relative movement of the inner and outer members are disclosed in U.S. Pat. Nos. 4,136,703, 4,381,013 and 5,728,148. The outer tubular member of the '013 patent enables the transmission of torque applied by the implanting physician at the proximal end to be transmitted to a fixation helix located at the lead body distal end lead to screwed the helix into endocardial tissue. Alternatively, two-piece stylets comprising a curved outer member and a relatively straight inner member are also known to the art, as disclosed in U.S. Pat. Nos. 4,676,249 and 5,040,543. In such composite stylets, the relative position of the inner member with respect to the outer member determines the degree to which the curved member (inner or outer) is allowed to display its preset curvature.

A common approach to providing controllable deflection of the distal end segments of catheters, guidewires, and stylets employs a generally straight outer sheath or tube and a pull or push or push-pull wire extending through a lumen of the outer sheath to an attachment point at the sheath distal end. The wire is pushed or pulled on at its proximal end typically through a handle that is permanently or removably attached to the catheter or guidewire proximal end. The proximal retraction or distal advancement of the pull or push wire, respectively, causes at least a distal segment of the outer sheath to bend or deflect. Examples of such deflection mechanisms in catheters can be found in U.S. Pat. Nos. 4,815,478, 4,898,577, 4,940,062, 5,545,200 and 6,251,092. U.S. Pat. Nos. 4,815,478 and 4,940,062 disclose the use of push-pull wires extending through guidewire lumens for deflecting a guidewire distal end by manipulating a handle at the guidewire proximal end.

Deflectable stylets intended to be inserted into cardiac lead body lumens employing this type of deflection mechanism are disclosed in U.S. Pat. Nos. 5,170,787, 5,327,906, 5,439,006, 5,662,119, 6,027,462, 6,059,739, and 6,146,338. Such deflectable stylets include an elongated stylet body or tube extending from a stylet body proximal end to a stylet body distal end, a handle coupled to the stylet body proximal end, and a traction wire or pull wire extending through a stylet lumen of the stylet body of tube from the handle to the stylet body distal end. Many of these patents disclose steerable stylet handles at the stylet body proximal end that are manipulated by one hand operation to induce a bend in a distal segment of the stylet body.

Several embodiments of deflectable stylets are disclosed in the '119 patent that employ an elongated metal tube having a stylet tube lumen through which a traction or pull wire extends to a distal wire end. In each case, a distal portion of the pull wire is exposed along a like distal portion of the metal tube in such a way that traction applied to the pull wire proximal end causes the distal portion of the tube to bow or bend. The exposure of the distal portion of the pull wire extending alongside the metal tube is created in several ways.

In one embodiment depicted in FIGS. 1 and 2 (FIGS. 12 and 13 of the '119 patent), an elongated cutaway portion 11' of the tube wall 15' of tube 10' is formed extending between cuts 18' and 20' proximal to tube distal end 22'. The cutaway portion 11' extends about half way through the tube wall 15' exposing a distal portion of the pull wire 12' extending proximally and distally through the tube lumen 13'. The pull wire 12' terminates in ball-shaped distal end element 23 having a diameter greater than the inside diameter of the tube lumen 13' that bears against the tube distal end 22' when pulled proximally.

In another embodiment depicted in FIG. 3 (FIG. 8 of the '119 patent), one side of the tube wall 15 is indented against the other side of the tube wall 15 between two openings 18 and 20 proximal to the tube distal end 22 to form a bendable indented portion 11 of the tube 10. The pull wire 12 is threaded out of the tube lumen 13 through the proximal opening 18 and back into the tube lumen 13 through the distal opening 20, whereby a distal portion of the pull wire 12 is exposed extending alongside the indented portion of the tube wall 15. The distal end of the pull wire 12 is crimped to the tube distal end 22 in this case.

The tube 10 is preferably formed of stainless steel hypodermic needle tubing having an outside diameter in the range of 0.012 to 0.016 inches. Pull wire 12 is preferably formed of high tensile strength stainless steel wire having a diameter in the range of 0.005 to 0.007 inches. The distance between the proximal openings 18, 18' and the distal openings 20, 20' is stated to be between 2 to 4 inches.

In a variation of these embodiments, a tubular retainer formed of a thin tube of polyimide, stainless steel or Nitinol is fitted over the tube 10 to extend across the indented portion 11 and the cutaway portion 11' to restrict the outward movement of the pull wire 12 when it is tensioned, which could exert excessive friction against the coiled conductors defining the cardiac lead lumen that the tube 10 is inserted into.

In use, the tube 10 is normally relatively straight when the pull wire 12 is relaxed. A curve or bend is effected in the distal portion of the tube 10 at the indented portion 11 or the cutaway portion 11' when the pull wire 12 is pulled proximally. The induced curve or bend stresses the tube wall 15 along the indented portion 11 and the cutaway portion 11'. It is stated in the '119 patent that prototypes of the cutaway tube embodiment of FIGS. 1 and 2 were found in testing to be inferior to the indented tube embodiment of FIG. 3 in resistance to kinking, and that the indented embodiment of FIG. 3 was easier to manufacture than the cutaway embodiment of FIGS. 1 and 2.

However, It can be difficult to indent thin wall stainless steel or shape memory alloy tubes to achieve the uniform indentation depicted in the '119 patent. It can also be difficult to precisely form uniform diameter proximal and distal holes as depicted in the '119 patent. Poor torque transmission and uneven bending characteristics can result particularly at the proximal end of the indented portion 11 that is weakened both by indentation and formation of the hole through the tube wall.

Thus, despite these improvements, there is still a perceived need for steerable stylet having a small diameter stylet body that is simple and inexpensive to manufacture, resists kinking, and that can be manipulated to control the deflection of and impart a wide degree of dynamic curvature in a distal segment of the stylet body.

SUMMARY OF THE INVENTION

The invention is therefore directed to improvements in a steerable elongated medical devices, adapted to be advanced through a tortuous pathway to a desired location and having a small diameter body that is simple and inexpensive to manufacture, resists kinking, and that can be manipulated easily to control the deflection of and impart a wide degree of dynamic curvature in a distal segment of the device.

In accordance with the present invention, a steerable elongated medical device adapted to be advanced through a tortuous pathway to a desired location in a body includes an outer tube extending between an outer tube proximal segment and an outer tube distal segment, having an outer tube wall forming an outer tube lumen and an elongated outer tube slot through the outer tube wall to the outer tube lumen. The elongated outer tube slot has a first portion and a second portion and is formed between an outer tube slot proximal end and an outer tube slot distal end and extending axially along the outer tube distal segment through an outer tube slot length to define a cutaway portion of the outer tube. A reinforcing sleeve is positioned within the outer tube lumen and extends between a reinforcing sleeve proximal end and a reinforcing sleeve distal end, and the reinforcing sleeve forms a reinforcing sleeve slot portion aligned with and extending along the first portion of the outer tube slot and includes a reinforcing sleeve overlap portion extending over the second portion of the outer tube slot.

According to an embodiment of the present invention, a steerable elongated medical device adapted to be advanced through a tortuous pathway to a desired location in a body includes an outer tube extending between an outer tube proximal segment and an outer tube distal segment, and having an outer tube wall forming an outer tube lumen and an elongated outer tube slot through the outer tube wall to the outer tube lumen. The elongated outer tube slot has a first portion and a second portion and is formed between an outer tube slot proximal end and an outer tube slot distal end and extends axially along the outer tube distal segment through an outer tube slot length to define a cutaway portion of the outer tube. A reinforcing sleeve is positioned within the outer tube lumen and extends between a reinforcing sleeve proximal end and a reinforcing sleeve distal end. The reinforcing sleeve forms a reinforcing sleeve slot portion aligned with and extending along the first portion of the outer tube slot and includes a reinforcing sleeve overlap portion extending over the second portion of the outer tube slot. A handle is coupled to the outer tube proximal end, and a pull wire is positioned within the outer tube lumen and extends between a pull wire proximal end coupled to the handle and a pull wire distal end coupled to the device along the outer tube distal end. The pull wire extends through the reinforcing sleeve lumen and the outer tube lumen, and the pull wire proximal end is adapted to be manipulated to separate the pull wire proximal end from the outer tube proximal end to induce a bend in the cutaway portion. The outer tube proximal segment is formed of a first material having a first flexibility and the outer tube distal segment is formed of a second material having a second flexibility different from the first flexibility In a preferred embodiment, the reinforcement sleeve has a reinforcement sleeve length that exceeds the length of the outer tube slot and is fitted into the outer tube lumen so that a reinforcement sleeve proximal segment extends proximally from the outer tube slot and a reinforcement sleeve distal segment extends distally from the outer tube slot. In a further feature of this embodiment, the reinforcement sleeve proximal segment is adhered to the outer tube lumen wall. In a still further feature of this embodiment, an elongated reinforcement sleeve intermediate segment extends the length of the outer tube slot. In yet another feature of this embodiment, at least a portion of the reinforcement sleeve intermediate segment is cut away to form an elongated reinforcement sleeve slot, and the outer tube slot and the reinforcement sleeve slot are aligned.

Preferably, a polymeric sleeve is fitted over the outer tube to extend over the aligned outer tube slot and reinforcement sleeve slot to retain the pull wire when the pull wire is retracted to form a bend in the nested outer tube and reinforcement sleeve walls.

Optionally, the pull wire can be formed having a taper along its length whereby the pull wire diameter extending through the aligned outer tube slot and reinforcement sleeve slot is less than the pull wire diameter proximal to the aligned outer tube slot and reinforcement sleeve slot.

Advantageously, the inclusion of the reinforcement sleeve resists the buckling encountered in testing the prior art steerable stylet design illustrated in FIGS. 1 and 2. Moreover, fabrication is simplified compared with the fabrication of prior art steerable medical devices.

The above-described steerable medical devices of the present invention advantageously facilitate the direct implantation of elongated cardiac leads having stylet lumens or the introduction and steering of guide catheters to a site of implantation of such cardiac leads or other medical devices or therapeutic or diagnostic substances. The features of the present invention can advantageously be incorporated into steerable stylets that impart or enhance torqueability and impart steerability to guide catheter distal ends.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 5 is a simplified top view of a distal segment of a stylet body formed having an elongated outer tube slot reinforced with an inner reinforcement sleeve in accordance with a first embodiment of the present invention;

FIG. 6 is a simplified side view of the distal segment of the stylet body of FIG. 5;

FIG. 7 is a simplified side view of a distal segment of a stylet body formed having an elongated outer tube slot reinforced with an inner reinforcement sleeve in accordance with a second embodiment of the present invention;

FIG. 8 is a cross-section view taken along lines 8—8 in FIG. 7.

The figures are not necessarily to scale.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. Although the present invention is described as preferably being applied to a steerable stylet, the aspects of the present invention are not intended to be limited to use in steerable stylets. Rather, it is understood that the present invention could be utilized in elongated medical devices other than steerable stylets, such as sheaths or catheters, for example. The preferred embodiments of the steerable stylets of the present invention can be employed within the lumens of endocardial cardiac leads, particularly endocardial pacing and/or cardioversion/defibrillation leads, but it will be understood that the steerable stylets of present invention can be utilized in any elongated medical instruments of the types described or mentioned herein and equivalents that may presently exist or come into existence in the future.

Moreover, the steerable stylets of the present invention can advantageously be fabricated in a relatively large diameter for use in directing introducers or guide catheters through tortuous pathways as described in the above-referenced '433 and '346 patents, for example, for implanting cardiac leads that do not have lead lumens. Steerable stylet bodies for insertion into cardiac lead lumens typically have a stylet body outer diameter of about 0.016 inches. Larger diameter steerable stylets having an outer diameter of 0.022 inches, for example, (incorporating the reinforcing sleeve construction of the present invention) can advantageously be employed in guide lumens of such bilumen catheters having a guide lumen diameter exceeding the typical cardiac lead body lumen diameter. It is easier to form smaller radii bends in the bendable distal sections of larger diameter (e.g., 0.022 inches) steerable stylet bodies than in smaller diameter (e.g., 0.016 inches) steerable stylets that are robust enough to bend the guide catheter shaft or body to substantially the same radii. Moreover, the larger diameter steerable stylet has sufficient torqueability to increase torqueability of certain guide catheter shafts or bodies or to impart torquebility to a guide catheter shaft or body lacking any torqueability. In addition, it is inherently easier and less expensive to fabricate such larger diameter steerable stylet bodies insertable into a guide lumen of a catheter body than to fabricate smaller diameter steerable stylets providing the same performance.

Figure 1:
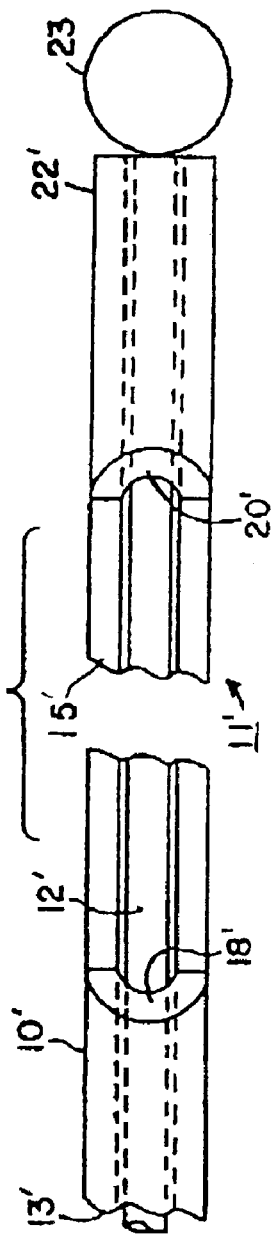
FIG. 1 is a simplified top view of a distal segment of a stylet body formed having a cutaway tube wall portion in accordance with the prior art.
Figure 2:
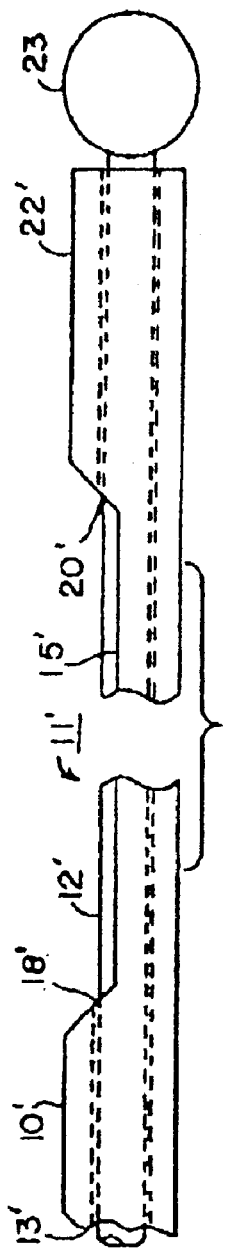
FIG. 2 is a simplified side view of the distal segment of a stylet body of FIG. 1 formed having a cutaway tube wall portion in accordance with the prior art.
Figure 3:
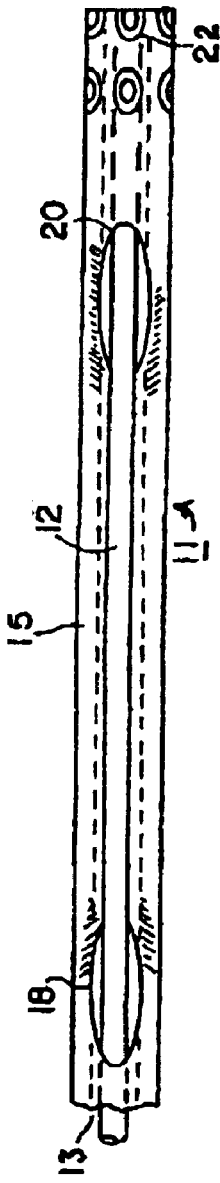
FIG. 3 is a simplified top view of a distal segment of a stylet body formed having a crushed tube wall portion in accordance with the prior art.
Figure 4:
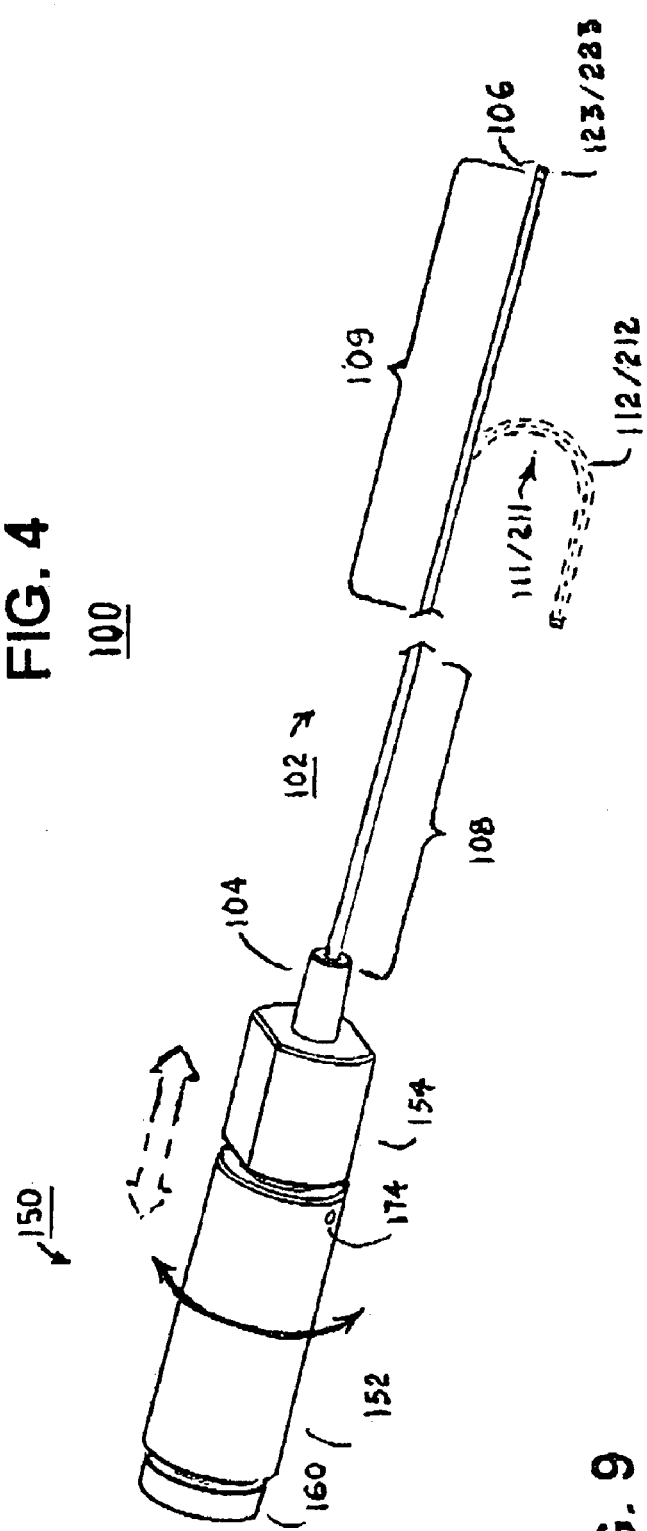
FIG. 4 is a simplified perspective view of a steerable stylet in which the present invention can be incorporated.

According to the present invention, an elongated medical instrument, such as a steerable stylet 100, that includes a handle 150 and an elongated stylet body 102 in which the embodiments and features of the present invention can advantageously be combined in various combinations is depicted in FIG. 4. The stylet body 102 extends a predetermined length between a stylet body proximal end 104 coupled to handle 150 and a stylet body distal end 106. The stylet body 102 further includes a stylet body proximal segment 108 and a stylet body distal segment 109. The stylet body 102 encloses an elongated pull wire 112/212 extending between a pull wire proximal end coupled to handle 150 and a pull wire distal end affixed at or near the stylet body distal end 106 or abutting a shoulder of the stylet body distal end 106. For example, the pull wire distal end is coupled to cylindrical distal pull wire stops 123/223 that abut a shoulder of the stylet body distal end 106 as described further below.

The stylet handle 150 includes a proximal handle portion 152 and a distal handle portion 154 that are movable from close proximity as depicted in FIG. 4 to separated apart positions to induce a bend in the stylet body distal segment 109. For example, the pull wire proximal end is coupled to the proximal handle portion 152 and the stylet body proximal end 104 is coupled to the distal handle portion 154. The pull wire extends distally to a stylet wire distal end that is coupled with the stylet body distal end 106. The user can grasp the proximal handle portion 152 with the thumb and index finger gripping the flattened sides of the distal handle portion 154. The distal handle portion 154 can be rotated with the fingers of the other hand to be moved away from the proximal handle portion 152. The pull wire attached to the proximal handle portion 152 is tensioned (but not twisted), and a bend, e.g., the 180° bend depicted in broken lines depicted in FIG. 4, can be induced in the stylet body distal segment 109 in a plane defined by the cutaway portion 111/211. While the term "pull wire" is used herein, it can be seen that in practice, the stylet body proximal end is pushed away from the pull wire proximal end. The induced bend remains even if the grip on the proximal and distal handle portions 152 and 154 is released.

A first preferred embodiment of the stylet body 102 is depicted in FIGS. 5 and 6. In this embodiment, an outer tube 110 extends the full length of the stylet body 102 through the proximal and distal segments 108 and 109 to an outer tube distal end 122. The outer tube 110 is preferably formed of stainless steel, hypodermic needle or "hypotube" or a shape memory alloy, e.g., NITi alloy or Nitinol alloy, having an outer diameter of 0.022 inches and an outer tube wall thickness, preferably 0.005 inches, providing an outer tube lumen 113 having an outer tube lumen diameter of 0.012 inches.

An elongated portion of the outer tube wall is cut away through an arc of 180° along a cutaway portion 111 near the stylet body distal end between outer tube slot proximal end 118 and outer tube slot distal end 120 to form an elongated outer tube slot 115, e.g., by grinding or EDM techniques. A reinforcement tube or sleeve 124 is fitted into the outer tube lumen 113 extending at least partly through the length of the outer tube slot 115. The reinforcement sleeve 124 has a reinforcement sleeve length extending between a reinforcement sleeve proximal end 132 and a reinforcement sleeve distal end 134, the length of the reinforcement sleeve 124 exceeding the length of the outer tube slot 115. The reinforcement sleeve 124, which is preferably formed of a shape memory alloy, forms a reinforcing sleeve lumen 127 so that reinforcing sleeve 124 has an outer diameter D1 of approximately 0.011 inches, for example, to fit the dimensions of the outer tube lumen 113, and an inner diameter D2 of approximately 0.008 inches, for example.

The reinforcement sleeve 124 is fitted into the outer tube lumen 113 so that a reinforcement sleeve proximal segment 142 extends proximally within outer tube lumen 113 from the proximal end 118 of the outer tube slot 115 and a reinforcement sleeve distal segment 146 extends distally within the outer tube lumen 113 from the distal end 120 of the outer tube slot 115. An elongated reinforcement sleeve intermediate segment 144 therefore extends the length of the outer tube slot 115. At least a portion 148 of the reinforcement sleeve intermediate segment 144 is cut away through 180° to form an elongated reinforcement sleeve slot 125 extending between reinforcement sleeve slot proximal end 128 and reinforcement sleeve slot distal end 130. The outer tube slot 115 and the reinforcement sleeve slot 125 are aligned, and the reinforcement sleeve proximal segment 142 is adhered to the wall of the outer tube lumen 113 to maintain the alignment. The adhesion can be effected employing Hysol® epoxy. The adhesion of the reinforcement sleeve proximal segment 142 to the wall of the outer tube lumen 113 allows the reinforcement sleeve intermediate and distal segments 144 and 146 free to slide along a wall of the outer tube lumen 113 when a bend is induced along the cutaway portion 111, such as by applying tension to the pull wire, for example. An overlap portion 117 of the reinforcement sleeve proximal to the reinforcement sleeve slot proximal end 128 and that extends within the outer tube slot 115 between reinforcement sleeve slot proximal end 128 and outer tube slot proximal end 118, provides strain relief bridging the outer tube slot proximal end 118 where buckling would otherwise likely take place.

In one example, the length of the reinforcement sleeve proximal segment 142 is approximately 0.100 inches, the length of the reinforcement sleeve intermediate segment 144 is approximately 0.750 inches, and the length of the reinforcement sleeve distal segment 146 is approximately 0.050 inches. The length of the reinforcement sleeve slot 125 is approximately 0.300 inches. The reinforcement sleeve distal end 134 is, at a minimum, approximately 0.100 inches from the outer tube distal end 122. The length dimensions and ratio of the length of the reinforcement sleeve slot 125 to the length of the reinforcement sleeve intermediate segment 144 and the outer tube slot 115 are be dependent upon the outer diameters, wall thicknesses, and materials of the outer tube and the reinforcement sleeve.

The ratio of the lengths of the solid wall reinforcement sleeve segments 142 and 146 and the ratio of the cut away reinforcement sleeve segment 148 with respect to the length of the outer tube slot 115 provide the optimal bending characteristics and resistance to kinking along the length of the outer tube slot 115. Stylet bodies having varying flexibility and possible shapes formed in the distal segments thereof can be achieved by controlling the dimensions of the outer tube slot 115 and the reinforcement sleeve slot 125. Generally, longer and deeper dimensions of the slots 115 and 125 increase flexibility but reduce rigidity in the cutaway portion 111. Thus, the dimensions of the slots 115 and 125 may be adjusted to provide the desired flexibility and rigidity of the cutaway portion 111 for the intended use.

In the illustrated embodiment, the slots 115 and 125 are shown to extend around the periphery of the outer tube 110 and the reinforcement sleeve 124 in an about 180° arc leaving intact arcuate tube walls of the outer tube 110 and reinforcement tube 124. The arc of the arcuate tube walls of the outer tube 110 and reinforcement tube 124 can differ from 180° and can differ from one another to achieve the desired flexibility and resulting bend shape.

The pull wire 112 extends through the reinforcement sleeve lumen 127 and the outer tube lumen 113 to a cylindrical distal pull wire stop 123. The distal end of the pull wire 112 is crimped into a lumen of a proximal extension of the distal pull wire stop 123 that fits into the outer tube lumen 113. The cylindrical distal pull wire stop 123 has an outer diameter approximately equal to the diameter of the outer tube 120, so that the cylindrical distal pull wire stop 123 bears against the outer tube distal end 122 when stressed. In this way, the pull wire distal end is "coupled" to the outer tube distal end 122 at the stylet body distal end 106 as indicated in FIG. 4. Optionally, the pull wire 112 can be formed having a taper along its length, whereby the pull wire diameter extending through the aligned outer tube slot 115 and reinforcement sleeve slot 125 is less than the pull wire diameter proximal to the aligned outer tube slot 115 and reinforcement sleeve slot 125. For example, the pull wire 112 can have a proximal wire diameter of 0.010 inches that is tapered to a distal wire diameter of 0.006 inches.

The shortened length of the cutaway portion 111 achieved by use of the reinforcement sleeve 124 also shortens the exposed length of the pull wire 112 so that it cannot extend as far away from the outer tube 110 when the outer tube 110 bows outward upon tensioning of the pull wire 112. Optionally, a polymeric outer sleeve 140 is fitted over the outer tube 110 to extend over the aligned outer tube slot 115 and reinforcement sleeve slot 125 to retain the pull wire 112 generally within the reinforcement sleeve lumen 127 when the pull wire 112 is retracted to form a bend in the nested outer tube and reinforcement sleeve walls. The polymeric outer sleeve 140 is formed of polyimide or PEEK, for example, that is fitted or adhered over the outer tube 110.

In these ways, the reinforcement sleeve 124 reinforces the wall of the outer tube 110 through at least a portion of the length of the outer tube slot 115 to prevent buckling when a bend is induced in the outer tube slot 115 and the reinforcement sleeve 124. In this way, when the elongated medical instrument includes a pull wire, a bend can be safely induced in the remaining arcuate section of the outer tube wall when the pull wire 112 extending through the outer tube lumen 113 is retracted with respect to the outer tube 110 (or the outer tube 110 is pushed distally with respect to the pull wire 112) by manipulation of the handle 150.

Referring again to FIG. 4, it is also possible to employ the principles of the present invention in a distal segment 109 of a stylet body 102 that is formed differently than the proximal segment 108 (or an intermediate segment) of the stylet body 102. The outer tube 110 can be replaced by a proximal outer tube segment and a distal outer tube segment formed of the same or differing materials, and having the same or differing wall outer tube diameters, wall thicknesses, and bending characteristics. The proximal and distal outer tube segments are joined together end-to-end, and the outer tube slot is formed in the tube wall of the distal tube segment.

For example, the proximal segment 108 of stylet body 102 is formed as shown in FIGS. 7 and 8 from a proximal outer tube 200 of stainless steel, e.g., 304W stainless steel alloy, that is joined at a junction 208 with a distal outer tube 210 that is formed of a shape memory alloy, e.g., Nitinol. Or the proximal segment 108 can be formed of a wire braid reinforced polymer tube.

In the depicted embodiment, the junction 208 is effected by an elongated distal counterbore 202 of the tube wall of the proximal outer tube 200 formed of stainless steel into which a proximal segment of the distal outer tube 210 is fitted and adhered employing epoxy cement or the like. A proximal outer tube lumen 204 is thereby axially aligned with a distal outer tube lumen 214. The proximal outer tube 200 preferably has an outer diameter of nominally 0.022 inches and an outer tube wall thickness of nominally 0.005 inches, providing an outer tube lumen 204 having a nominal outer tube lumen diameter of 0.012 inches. The counterbore diameter is preferably nominally 0.017 inches to receive a distal outer tube 210 having an outer diameter of nominally 0.016 inches and a distal outer tube lumen nominal diameter of 0.011 inches.

An elongated portion of the distal outer tube wall is cut away through 180° near the stylet body distal end between distal outer tube slot proximal end 218 and distal outer tube slot distal end 220 to form an elongated outer tube slot 215. Thus, an intact proximal tubular portion of the distal outer tube 210 extends proximally from the distal outer tube slot proximal end 218, and an intact distal tubular portion of the distal outer tube 210 extends distally from distal outer tube slot distal end 220.

A tubular distal reinforcement tube or sleeve 224 is fitted into the distal outer tube lumen 214 extending at least partly through the length of the distal outer tube slot 215. The reinforcement sleeve 224 is preferably formed of a shape memory alloy and has an outer sleeve outer diameter of 0.016 inches, for example, and a reinforcement sleeve lumen 227 inner sleeve lumen diameter of 0.105 inches, for example.

The reinforcement sleeve 224 has a reinforcement sleeve length extending between a reinforcement sleeve proximal end 232 and a reinforcement sleeve distal end 234. In this embodiment, the reinforcement sleeve 224 is tubular and does not have an elongated slot cut away leaving an arcuate section of the tubular wall. And, the reinforcement sleeve 224 does not exceed the length of the outer tube slot 215, whereby the reinforcement sleeve distal end 234 is disposed intermediate the distal outer tube slot proximal end 218 and distal outer tube slot distal end 220. For example, the distal outer tube slot 215 can have a nominal length of 1.500 inches, and the reinforcement sleeve distal end 234 is disposed nominally at 0.375 to 0.750 inches from the distal outer tube slot proximal end 218 and distal outer tube slot distal end 220.

The pull wire 212 extends through the reinforcement sleeve lumen 227, the distal outer sleeve lumen 214 and the proximal outer sleeve lumen 204 to a cylindrical distal pull wire stop 223. The distal end of the pull wire 212 is crimped into a lumen of the distal pull wire stop 223. The cylindrical distal pull wire stop 223 has an outer diameter that exceeds the distal outer tube lumen 214 and bears against the distal outer tube distal end 216 when stressed. Optionally, the pull wire 212 can be formed having a taper along its length, whereby the pull wire diameter extending through the distal outer tube slot 215 and reinforcement sleeve lumen 227 is less than the pull wire diameter within the proximal outer tube lumen 204. For example, the pull wire 212 can have a proximal wire diameter of 0.010 inches that is tapered to a distal wire diameter of 0.006 inches.

Optionally, a polymeric outer sleeve 240 is fitted over the distal outer tube 210 to extend over the aligned distal outer tube slot 215 and the reinforcement sleeve 224 to retain the pull wire 212 generally within the distal outer tube lumen 214 when the pull wire 212 is retracted to form a bend in the distal outer tube 210 and the reinforcement sleeve 224 in the cutaway portion 211. The polymeric outer sleeve 140 can comprise polyimide or PEEK that is fitted or adhered over the outer tube 110.

In these ways, the reinforcement sleeve 224 reinforces the wall of the distal outer tube 210 across the outer tube slot proximal end 218 and through at least a portion 246 of the full length 244 of the distal outer tube slot 215 to prevent buckling when a bend is induced in the distal outer tube 210 and the reinforcement sleeve 224 in the cutaway portion 211. A bend can be safely induced in the arcuate section of the distal outer tube wall when the pull wire 212 extending through the aligned lumens is retracted with respect to the proximal and distal outer tubes 200 and 210 (or the outer tubes 200 and 210 are pushed distally with respect to the pull wire 212) by manipulation of handle 150.

Again, the characteristics of the induced bend can be altered by the selection of the length 244 of the cutaway portion 211, and the ratio of the segment length 246 to the full length 244 of the cutaway portion 211. It should be noted that the reinforcement sleeve 224 can be shaped in the same manner as slotted reinforcement sleeve 124 described above with respect to FIGS. 5 and 6.

Referring again to FIG. 4, the stylet handle 150 can take any form that enables the application of tension between and to separate the proximal end of the pull wire 112/212 and the stylet body proximal end 104 apart to steer the stylet body distal end 106 and induce a bend along the cutaway portions 111/211.

Figure 9:
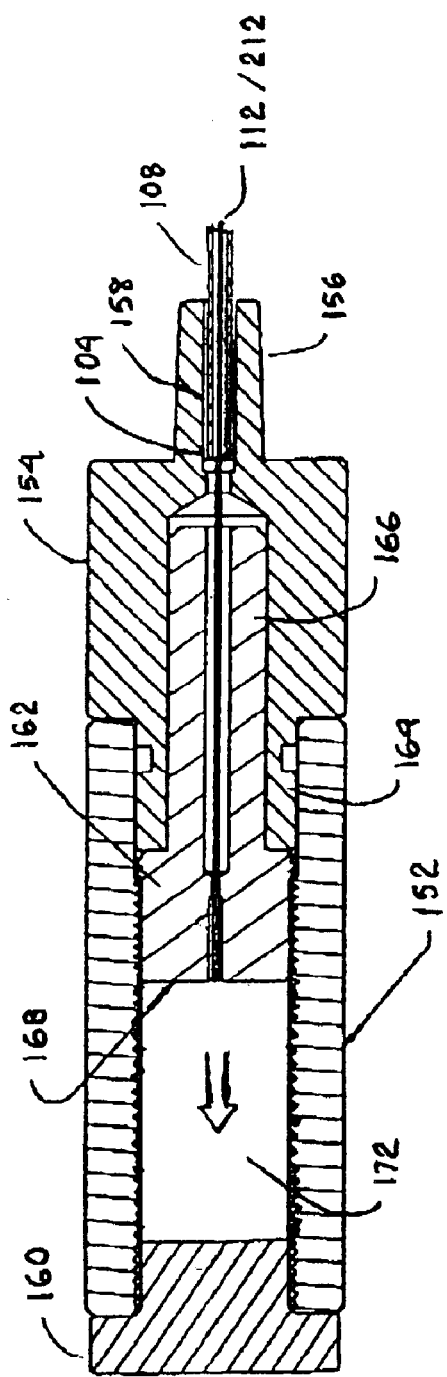
FIG. 9 is a cross-section view taken along lines 9—9 in FIG. 4 of a preferred stylet handle.

A particular configuration of the stylet handle 150 is shown in FIG. 9. The distal handle portion 154 has a tubular distal projection 156 into which the stylet body 104 is inserted and attached by adhesive. A distal handle portion lumen 158 extends through the distal handle portion 154. The proximal handle portion 152 is tubular and threaded internally within proximal handle portion lumen 172 at its distal end to receive a handle end cap 160 and threaded more proximally to receive the threads on the distal projection 168 of a handle insert 162 to enable the handle insert 162 to be moved proximally to release tension or distally to increase tension on the pull wire 112/212. The proximal end opening of the proximal handle portion 152 receives a tubular proximal projection 164 of the distal handle portion 154.

The handle insert 162 comprises a handle insert proximal projection 166 extending into the distal handle portion lumen 158 and a threaded handle insert distal projection 168 that is attached to the internal threads of the proximal handle portion 152. The pull wire 112/212 is inserted through a handle insert lumen 170 that is axially aligned with the distal handle portion lumen 158 extending through the tubular distal projection 156. The proximal end of the pull wire 112/212 is attached to the handle insert 162.

One side of the handle insert distal projection 166 is flattened and bears against a guide pin 174 extending across the proximal handle lumen 172. A groove 176 is formed around the tubular proximal projection 164 to track a further guide pin (not shown). The user grips the sides of the distal handle portion 154 and rotates the proximal handle portion 152 to rotate the internal screw threads around lumen 172 with respect to the mating screw threads around handle insert distal projection 168 to move handle insert 162 proximally. The proximal movement tensions the pull wire 112/212 and induces the bend 111/211 as described above. Advantageously, the handle 150 is light in weight, and the tension and induced bend remains in place even if the handle 150 is released so that the user can manipulate the guide catheter handle without having to focus on manually maintaining the bend.

The above-described steerable stylets advantageously facilitate the direct implantation of elongated cardiac leads having stylet lumens or the introduction and steering of guide catheters to a site of implantation of such cardiac leads or other medical devices or therapeutic or diagnostic substances.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of steerable stylets with elongated medical leads or guide catheters or other elongated medical instruments that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

What is claimed is:

1. A steerable elongated medical device adapted to be advanced through a tortuous pathway to a desired location in a body, comprising:

an outer tube extending between an outer tube proximal segment and an outer tube distal segment, having an outer tube wall forming an outer tube lumen and an elongated outer tube slot through the outer tube wall to the outer tube lumen, the elongated outer tube slot having a first portion and a second portion and formed between an outer tube slot proximal end and an outer tube slot distal end and extending axially along the outer tube distal segment through an outer tube slot length to define a cutaway portion of the outer tube;

a reinforcing sleeve positioned within the outer tube lumen and extending between a reinforcing sleeve proximal end and a reinforcing sleeve distal end, wherein the reinforcing sleeve forms a reinforcing sleeve slot portion aligned with and extending along the first portion of the outer tube slot and includes a reinforcing sleeve overlap portion extending over the second portion of the outer tube slot.

2. The device of claim 1, wherein the reinforcing sleeve includes a reinforcing sleeve proximal segment extending proximally within the outer tube lumen from the outer tube slot proximal end, a reinforcing sleeve distal segment extending distally within the outer tube lumen from the outer tube slot distal end, and a reinforcing sleeve intermediate segment extending between the reinforcing sleeve proximal segment and the reinforcing sleeve distal segment, and wherein the reinforcing sleeve is fixedly engaged within the outer tube lumen along the reinforcing sleeve proximal segment and both the reinforcing sleeve intermediate segment and the reinforcing sleeve distal segment advance freely along the outer tube wall In response to a bend being induced at the cutaway portion.

3. The device of claim 2, wherein the reinforcement sleeve slot portion extends between a reinforcement sleeve slot proximal end and a reinforcement sleeve slot distal end and the reinforcing sleeve overlap portion extends between the outer tube slot proximal end and the reinforcement sleeve slot proximal end.

4. The device of claim 1, further comprising means for attaching the reinforcing sleeve to the outer tube wall proximal to the outer tube slot proximal end.

5. The device of claim 1, wherein the reinforcing sleeve forms a reinforcing sleeve lumen extending between the reinforcing sleeve proximal end and the reinforcing sleeve distal end, the device further comprising:

a handle coupled to the outer tube proximal end; and a pull wire positioned within the outer tube lumen and extending between a pull wire proximal end coupled to the handle and a pull wire distal end coupled to the device along the outer tube distal end, the pull wire extending through the reinforcing sleeve lumen and the outer tube lumen, wherein the pull wire proximal end is adapted to be manipulated to separate the pull wire proximal end from the outer tube proximal end to induce a bend in the cutaway portion.

6. The device of claim 5, further comprising a polymeric sleeve fitted over the outer tube extending over the aligned outer tube slot and the reinforcing sleeve overlap portion to retain the pull wire when the pull wire is retracted to form a bend in the cutaway portion.

7. The device of claim 6, wherein the reinforcing sleeve has a reinforcing sleeve length extending between the reinforcing sleeve proximal end and the reinforcing sleeve distal end that is greater than the outer tube slot length, and the reinforcing sleeve overlap portion includes a sleeve distal segment distal to the outer tube slot distal end and a sleeve intermediate segment extending the length of the outer sleeve slot.

8. The device of claim 5, wherein the outer tube wall is cut away through an arc of approximately 180° to form the outer tube slot.

9. The device of claim 8, further comprising a polymeric sleeve fitted over the outer tube extending over the aligned outer tube slot and reinforcing sleeve slot portion and the reinforcing sleeve overlap portion to retain the pull wire when the pull wire is retracted to form a bend in the cutaway portion.

10. The device of claim 9, wherein the reinforcing sleeve slot portion has a reinforcing sleeve slot length extending between a reinforcement sleeve slot proximal end and a reinforcement sleeve slot distal end that is approximately fifty percent of the outer tube slot length.

11. The device of claim 1, wherein the reinforcing sleeve is formed of a shape memory alloy.

12. The device of claim 1, wherein the reinforcing sleeve overlap portion has a length that is a fraction of the outer tube slot length.

13. The device of claim 1, wherein the reinforcing sleeve overlap portion has a length that is approximately fifty percent of the outer tube slot length.

14. The device of claim 13, wherein the reinforcing sleeve is cut away through an arc of approximately 180° to form the reinforcing sleeve slot portion.

15. The device of claim 14, wherein the reinforcing sleeve slot portion has a reinforcing sleeve slot length extending between a reinforcement sleeve slot proximal end and a reinforcement sleeve slot distal end that is approximately fifty percent of the outer tubs slot length.

16. The device of claim 1, wherein the device is insertable within a bilumen guide catheter having a guide lumen for receiving the device and a delivery lumen for receiving an elongated electrical medical lead body for implantation at a cardiac site.

* * * * *